United States Patent [19]

Kimmelstiel

[11] Patent Number: 5,325,868
[45] Date of Patent: Jul. 5, 1994

[54] SELF-GRIPPING MEDICAL WIRE TORQUER

[76] Inventor: Carey D. Kimmelstiel, 47 Overlook Dr., Framingham, Mass. 01701

[21] Appl. No.: 57,703

[22] Filed: May 4, 1993

[51] Int. Cl.⁵ .............................................. A61B 5/00
[52] U.S. Cl. ........................................ 128/772; 604/95
[58] Field of Search ............... 128/657, 772; 604/95, 604/117, 159, 280; 606/180, 225

[56] References Cited

U.S. PATENT DOCUMENTS

| | | | |
|---|---|---|---|
| 4,380,433 | 4/1983 | Ellman et al. | 433/87 |
| 4,509,233 | 4/1985 | Shaw | 24/115 M |
| 4,726,369 | 2/1988 | Mar | 128/657 |
| 4,829,999 | 5/1989 | Ruth | 24/115 R |
| 4,858,810 | 8/1989 | Intlekofer et al. | 24/115 M |
| 5,161,534 | 11/1992 | Berthiaum | 128/657 |
| 5,219,332 | 6/1993 | Nelson et al. | 128/657 |

Primary Examiner—Max Hindenburg
Attorney, Agent, or Firm—Joseph S. Iandiorio

[57] ABSTRACT

A self-gripping wire torquer including a sleeve body, a clamping device biased for automatically grasping the wire and releasably fixing the sleeve body in place on the wire, and a release mechanism for temporarily releasing the clamp means to slide and reposition the torquer along the wire.

27 Claims, 2 Drawing Sheets

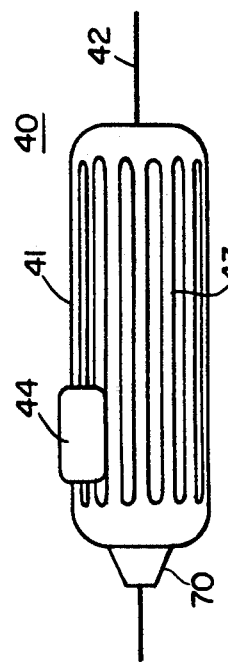
FIG. 1 PRIOR ART
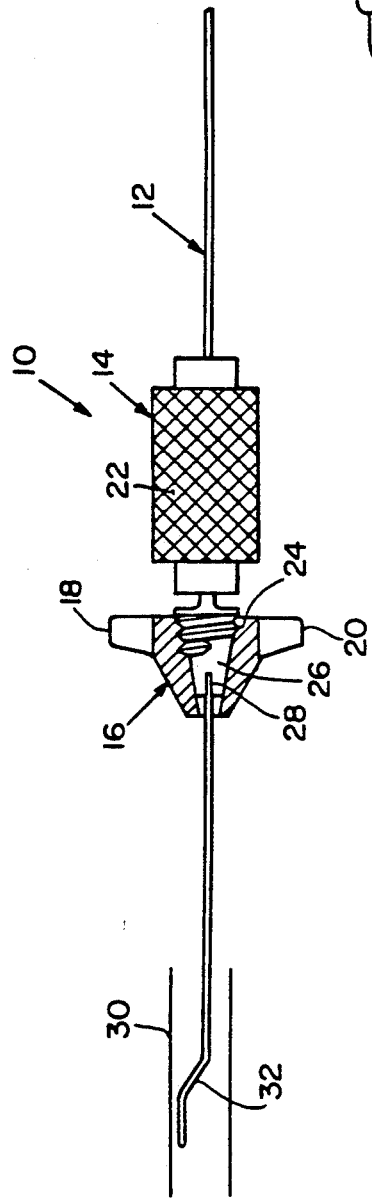
FIG. 2
FIG. 3B
FIG. 3A

SELF-GRIPPING MEDICAL WIRE TORQUER

FIELD OF INVENTION

This invention relates to a one handed self-gripping wire torquer device for use in maneuvering a guide wire used in angioplasty and other vascular procedures.

BACKGROUND OF INVENTION

Recent studies have suggested that the angioplasty procedure is superior to medication alone for relieving angina in selected patients. The angioplasty procedure has been shown to reduce symptoms in patients with coronory artery disease as well as in patients with peripheral vascular disease as well as being useful adjunct in patients experiencing an acute myocardial infarction.

During angioplasty and related procedures, a guidewire is inserted into an artery and maneuvered to the site of the stenosis. Since the guidewire is relatively fine and difficult to grip between the fingers, a device called a "torquer" is affixed to the wire and used to twist the wire to negotiate the various turns and branches in the coronary arteries. As might be expected, the angioplasty procedure requires precision and intense continuous concentration on the part of the surgeon.

Current torquers suffer from various disadvantages the most notable of which is that since the torquer must be manually locked onto the wire, repositioning the torquer from a locked position at one place on the wire to a locked position at another place on the wire is a two-handed operation. Conventional torquers employ a locking nut portion, which, when turned in one direction causes the torquer to lock onto the wire; and which, when turned in the opposite direction releases the torquer so that it may freely slide along the wire. Unlocking this type of torquer, moving it along the wire, and locking it in place is a tow-handed operation requiring the surgeon's full attention and generally necessitates a period of time when non-visualization of the patents coronary anatomy occurs. Hence, the physician's attention is directed away from fluoroscopy video monitoring equipment and hemodynamic monitoring equipment.

Since it is often a lengthy and arduous process to properly position the wire in the patient's artery, a loss of registration or position while the surgeon repositions the torquer on the wire is costly in the sense of loss of the physician's time, and also potentially painful, uncomfortable and subject to acute vascular complications in patients undergoing the procedure.

Another tool for steering an angioplasty guide wire includes a body of resilient material with a slit in which the guide wire is received. Therefore, the tool can be attached to the wire from the side. An outer sleeve encircles the resilient body and may be used to compress the resilient body holding the slit closed to grip the wire tightly. This tool, however, suffers from the same problem as conventional torquers: repositioning the tool on the wire requires pulling the wire out of the slit, repositioning the tool on the wire, and finally pressing the wire back into the slit. As delineated above, such a time consuming, two-handed operation is adverse to an efficient angioplasty procedure.

Finally, when these conventional torquers are released from the wire, a process which may be performed two to three times to reposition the torquer during the angioplasty procedure, the turning motion used to separate the torquer from the wire is transmitted to the wire itself causing the end of the wire to turn in the artery and even jerk slightly. Hence, a loss of registration can occur further interfering with the expeditious performance of the angioplasty procedure and possibly causing procedure lengthening and patient discomfort.

SUMMARY OF THE INVENTION

It is therefore an object of this invention to provide a wire torquer which is automatically self gripping and which can therefore be repositioned on the guide wire using only one hand.

It is a further object of this invention to provide such a wire torquer which can be smoothly and effortlessly slid along the wire during repositioning without jerking or turning the wire.

It is a further object of this invention to provide such a wire torquer which can be repositioned without adversely affecting the concentration of the surgeon.

It is a further object of this invention to provide such a wire torquer which can be locked in place, unlocked, slid along, and then locked again in place on the guide wire faster and easier than torquers employing locking nuts.

It is a further object of this invention to provide such a wire torquer which can be fabricated using inexpensive components and fabrication processes.

It is a further object of this invention to provide such a wire torquer which can be disengaged from the wire without turning the wire thereby preventing a loss of registration of the wire within the artery.

This invention results from the realization that a one-handed self-gripping wire torquer can be achieved with a clamping device biased to automatically grip the wire and with a sleeve body which allows releasing the clamping device with one hand thereby facilitating easy and smooth repositioning of the torquer along the wire without the need for the surgeon to divert his or her attention from the angioplasty process.

This invention features a self-gripping wire torquer including a sleeve body, clamp means biased for automatically grasping the wire and releasably fixing the sleeve body in place on the wire, and means for temporarily releasing the clamp means to slide and reposition the torquer along the wire. The clamp means may include opposing members biased for mating about the wire one of which is pivotable and biased by at least one spring. An actuator, disposed for rotating the pivotable member and compressing the spring, such as a button depressible within a channel in the sleeve body, facilitates one-handed operation of the wire torquer of this invention. The pivotable member may include raised gripping teeth and the opposing stationary member may include complementary recesses associated with each raised gripping tooth. The sleeve body may include a knurled surface for assisting in gripping the sleeve body. The sleeve body may be tubular and even barrel shaped and include a constricting tip portion on at least one end.

This invention also features a self-gripping wire torquer comprising a sleeve body and an internal chuck including at least two opposing gripping members biased by a circumferential coil spring. The spring may include distending end portions for releasing the gripping members from the wire when compressed. In this embodiment, sleeve body is resilient and compressible about the distending end portions of the coil spring.

This invention also features a self-gripping wire torquer including a barrel shaped sleeve body having a constricting tip portion on at least one end and a passage for receiving the wire, and a clamp integral with the sleeve body including at least two opposing member biased for mating about the wire for grasping the wire and releasibly fixing the sleeve body in place on the wire. Release means are included for temporarily releasing the opposing members about the wire for sliding or repositioning the sleeve body along the wire. One of the opposing members may be pivotable within the sleeve body and biased with respect to its associated opposing member by at least one spring. An actuator rotates the pivotable member and simultaneously compresses the spring allowing repositioning of the sleeve body along the wire.

This invention also features a resilient sleeve body having a passage for receiving the wire, and a chuck within the sleeve body biased for grasping the wire temporarily releasable upon compression of the sleeve body for sliding the sleeve body along the wire. The chuck may include opposing members separated by slits formed partially along the length of the chuck and a circumferential coil spring about the opposing members for compressing the opposing members about the wire. The coil spring may include distending end portions extending outwardly from the opposing members for relaxing the spring when compressed.

DISCLOSURE OF A PREFERRED EMBODIMENT

Other objects, features and advantages will occur to those skilled in the art from the following description of a preferred embodiment and the accompanying drawings, in which:

FIG. 1 is a schematic diagram of a prior art wire torquer;

FIG. 2 is a side view of a wire torquer according to this invention;

FIG. 3A is an enlarged, sectional side view of the wire torquer of FIG. 2 showing the internal clamping mechanism;

FIG. 3B is an enlarged side view of a portion of the internal clamping mechanism of FIG. 3A;

Figure 4:
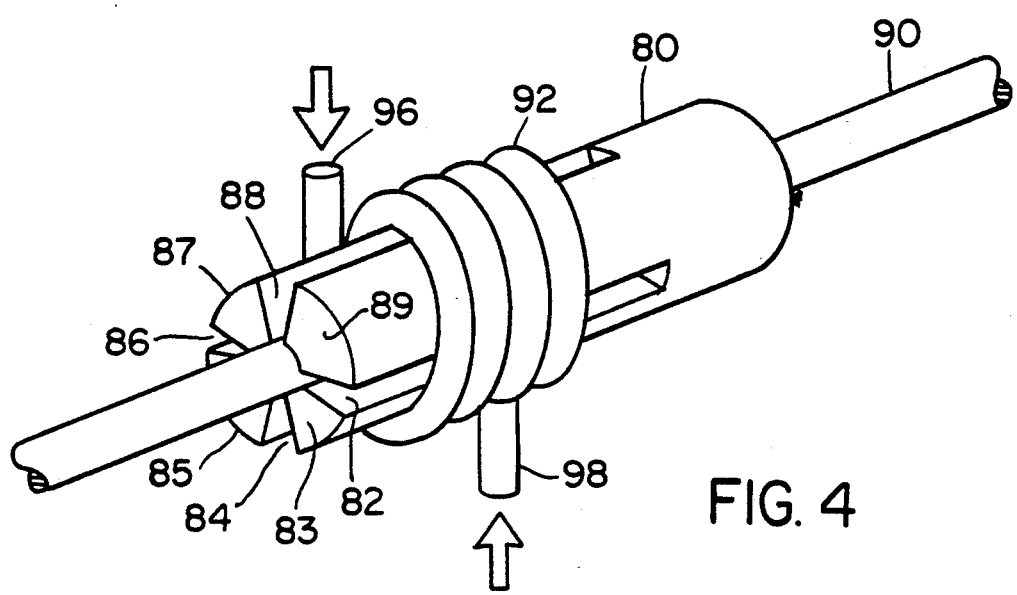
FIG. 4 is a three dimensional schematic diagram of a spring biased chuck that may be incorporated in an embodiment of a wire torquer according to this invention.

The self-gripping wire torquer of this invention may be accomplished by a sleeve body with an internal passage for receiving the wire to be introduced and maneuvered within an artery. Clamp means internal to the sleeve body and biased for automatically grasping the wire, releasably fix the sleeve body in place on the wire. The clamp means may include two opposing members, one of which is pivotable and biased by one or more springs for mating with the opposing fixed member about the wire. In this embodiment, an actuator in the form of a button depressible within a channel in the sleeve body rotates the pivotable member simultaneously compressing the springs to allow the sleeve body to be slid along the wire smoothly using only one finger or the thumb. In another embodiment, the clamp means includes a chuck biased for gripping the wire by a circumferential coil spring.

Contrary to this invention, prior art torquer device 10, FIG. 1 requires two hands for repositioning torquer 10 along wire 12. Torquer 10, mounted on wire 12, includes a body 14 and a nut 16 having ears 18 and 20 which can be gripped with one hand while the knurled surface 22 of body 14 is gripped with the other. When body 14 is held fast and nut 16 is rotated in one direction (or vice versa), nut 16 moves on threads 24 in a direction away from body 14. This permits nose piece 26 to spread open by virtue of splits 28, releasing pressure on wire 12 so that the entire wire torquer 10 can be slid forward or backward on wire 12. Wire torquer 10 is then repositioned, nut 16 is tightened, and slots 28 of nosepiece 16 again pinch wire 12 and hold torquer 10 in place on wire 12 for assisting in negotiating the wire through the various turns and branches of artery 30.

A serious disadvantage of torquer device 10, as discussed in the Background of the Invention above, is that the surgeon must use two hands to reposition torquer 10 along wire 12. Moreover, turning nut 16 or body 14 often results in turning or even jerking wire 12. Since the portion of wire 12 in the artery 30 includes bend 32, if wire 12 turns, a loss of registration can occur or worse wire 12 may scrape the wall of artery 30. The most important disadvantage, however, is that repositioning prior art torquer 10 steals the surgeon's attention away from critical monitoring equipment resulting in a loss of critical time and position during the angioplasty procedure.

Torquer 40, FIG. 2, according to this invention includes tubular barrel shaped sleeve body 41, tip portion 70, and clamp means (shown in FIGS. 3A & 3B) biased for automatically gripping wire 42. An actuator in the form of button 44, depressible with one finger or the thumb, releases the clamp means and allows smooth and easy repositioning of torquer 40 along the wire. In this way, the surgeon may depress button 44 and maneuver torquer 40 while still supervising the operation and associated monitoring devices such as angioscopy video monitoring equipment and fluoroscopy monitors. And, repositioning torquer 40 along wire 42 does not turn or jerk wire 42 as with prior art devices. Sleeve body 41 may include knurled surface 43 for better gripping by the surgeon.

In operation, one end of guidewire 42 is inserted through one side arm of a dilation catheter (not shown) and then into an artery. Torquer 40 is then slid onto the opposite end while button 44 is depressed. Constricting tip 70 aids in threading wire 42 through torquer 40. Guidewire 42 is then used to negotiate the various turns and branches in the coronary arteries. At various times during this procedure, torquer 40 must be repositioned when a greater length of wire 42 must be inserted into the artery. Accordingly, the surgeon depresses button 44 with a finger or the thumb, slides torquer 12 backwards along the wire, and releases button 44 for a positive automatic grip of wire torquer 40 on wire 42. Hence, repositioning is a smooth one-handed operation, the wire does not turn during repositioning, and no loss of registration or diversion of the surgeon's attention occurs.

Torquer 40, FIG. 3A comprises clamp means which may include opposing pivotable member 46 and stationary member 48. Pivotable member 46 is biased by springs 50 and 52 tending to force pivotable member 46 to mate with stationary member 48, automatically gripping wire 42 therebetween in the non-released position. Pressure on button 44, which is depressible within channel 47 of sleeve body 41, moves member 54 downward behind wire 42 to disengage the mating surface of pivotable member 46 from wire 42. Then, with button 44 still depressed, wire torquer 40 may be moved forward or backward along wire 42.

Pivotable member 46 may include one or more raised gripping teeth 56, 58, 60 and stationary member 48 may include complementary recesses 62, 64 and 66 for an enhanced grip on wire 42. Also, tooth 68, proximate constricting tip 70, of sleeve body 41 assists in assuring a positive grip on wire 42. Gripping tooth 60 is shown in FIG. 3B. When pivotable member 46 is maneuvered downward, wire 42 is free to slide proximate stationary member 48 as shown. Other equivalent means of positively gripping wire 42, however, are within the scope of this invention.

Figure 5:
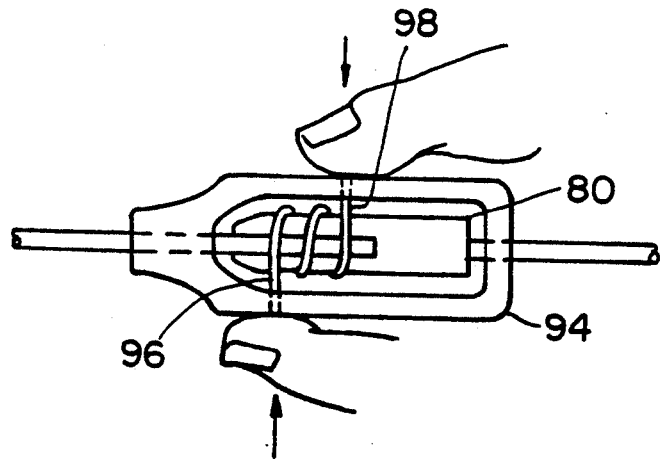
FIG. 5 is a schematic diagram of a sleeve body encapsulating the spring biased chuck of FIG. 4.

For example, chuck 80, FIG. 4, including slots 82, 84, 86, and 88 separating opposing gripping members 83, 85, 87, and 89 may be automatically biased for gripping wire 90 by coil spring 92. Coil spring tends to automatically pivot members 83, 85, 87, and 89 towards each other ensuring a firm grip on wire 90 disposed therebetween. Compressible sleeve body 94, FIG. 5, made of a resilient material, encompasses chuck 80, and when squeezed by the surgeon's fingers, places pressure on distending spring ends 96 and 98 to release chuck 80 from wire 90 again allowing a simplified one-handed operation. When spring 92 is relaxed, opposing gripping members 83, 85, 87, and 89, FIG. 4 are not engaged wire 90 and hence allow free passage of wire 90 through sleeve body 94. Alternatively, spring 92 could be double-wound to achieve the same function.

Others skilled in the art will recognize other related and equivalent configurations in which clamp means are automatically biased for gripping the wire and released by mechanical linkages integral with a tubular shaped sleeve body or otherwise released by manipulating or compressing the sleeve body in some fashion. Moreover, the use of this invention on a guidewire is not a limitation of the following claims. Use of this device with other tubing and similar lengthy slender members used in angioplasty and other procedures using catheters and the like is understood to be within the following claims.

Although specific features of the invention are shown in some drawings and not others, this is for convenience only as some feature may be combined with any or all of the other features in accordance with the invention.

Other embodiments will occur to those skilled in the art and are within the following claims.

What is claimed is:

1. A self-gripping medical wire torquer comprising:
   a sleeve body;
   separate clamp means within said sleeve body, biased for automatically grasping a wire and releasably fixing said sleeve body in place on the wire; and
   release means, for temporarily releasing said clamp means to slide and reposition the torquer along the wire.

2. The wire torquer according to claim 1 in which said clamp means includes opposing members biased for mating about the wire.

3. The wire torquer according to claim 2 in which at least one of said opposing members is pivotable and biased for mating with an opposing member by at least one spring.

4. The wire torquer of claim 3 in which said release means includes an actuator disposed for rotating said pivotable member and compressing said spring.

5. The wire torquer of claim 4 in which said actuator includes a button depressible within a channel in said sleeve body.

6. The wire torquer of claim 3 in which said pivotable member includes at least one gripping raised tooth.

7. The wire torquer of claim 6 in which said member opposing said pivotable member includes at least one complementary recess associated with said gripping raised tooth.

8. The wire torquer of claim 1 in which said sleeve body includes a knurled surface for assisting in gripping said sleeve body.

9. The wire torquer of claim 1 in which said sleeve body includes a barrel portion and a constricting tip portion on at least one end.

10. The wire torquer of claim 1 in which said clamp means includes a spring biased chuck for releasably engaging and gripping the wire.

11. The wire torquer of claim 10 in which said chuck includes at least two opposing separated gripping members biased for engaging the wire by a circumferential coil spring.

12. The wire torquer of claim 11 in which said release means includes distending end portions of said coil spring for releasing said gripping members from the wire when compressed.

13. The wire torquer of claim 12 in which said sleeve body is compressible about said distending end portions of said coil spring.

14. A self-gripping medical wire torquer comprising:
   a tubular shaped sleeve body having a constricting tip portion on at least one end and a passage for receiving the wire;
   separate clamp means, integral within said sleeve body, including at least two opposing members biased for automatically mating about the wire for grasping the wire and releasably fixing said sleeve body in place on the wire; and
   release means for temporarily releasing said opposing members from the wire for sliding and repositioning said sleeve body along the wire.

15. The wire torquer of claim 14 in which at least one said member is pivotable within said sleeve body, said pivotable member biased with respect to its associated opposing member by at least one spring.

16. The wire torquer of claim 15 in which said release means includes an actuator for rotating said pivotable member and compressing said spring.

17. The wire torquer of claim 14 in which at least one of said opposing members includes raised gripping teeth.

18. The wire torquer of claim 14 in which said clamp means includes a chuck the distal end of which includes opposing members separated by slits formed partially along the length of said chuck.

19. The wire torquer of claim 18 in which said opposing members are biased for engaging the wire passing therebetween by a circumferential coil spring.

20. An self-gripping medical wire torquer comprising:
   a resilient sleeve body having a passage for receiving the wire; and
   a chuck within said sleeve body spring biased for automatically grasping the wire, and temporarily releasable upon compression of said sleeve body for sliding the sleeve body along the wire.

21. The wire torquer of claim 20 in which said chuck includes opposing members separated by slits formed partially along the length of the chuck.

22. The wire torquer of claim 21 in which said chuck includes a circumferential coil spring about said opposing members for compressing said opposing members about the wire.

23. The wire torquer of claim 22 in which said circumferential coil spring includes distending end portions extending outwardly from said opposing members for relaxing said spring when compressed.

24. A self-gripping medical wire torquer comprising:
a sleeve body;
clamp means including opposing members biased by at least one spring for mating about the wire, at least one of said opposing members pivotable for automatically grasping the wire and releasably fixing said sleeve body in place on the wire; and
release means, for temporarily releasing said clamp means to slide and reposition the torquer along the wire.

25. A self-gripping medical wire torquer comprising:
a sleeve body;
clamp means including a spring biased chuck for releasably engaging and gripping the wire releasably fixing said sleeve body in place on the wire; and
release means, for temporarily releasing said chuck to slide and reposition the torquer along the wire.

26. A self-gripping medical wire torquer comprising:
a tubular shaped sleeve body having a constricting tip portion on at least one end and a passage for receiving the wire;
clamp means integral within said sleeve body, including at least two opposing members, one said member pivotable within said sleeve body, said pivotable member biased with respect to its associated opposing member for automatically mating about the wire for grasping the wire and releasably fixing the sleeve body in place on the wire; and
release means for temporarily releasing said opposing members from the wire for sliding and repositioning the sleeve body along the wire.

27. A self-gripping medical wire torquer comprising:
a resilient sleeve body having a passage for receiving the wire; and
a chuck including opposing members separated by slits formed partially along the length of the chuck and a circumferential coil spring about said opposing members for compressing said opposing members about the wire for automatically grasping the wire, and temporarily releasable upon compression of said sleeve body for sliding the sleeve body along the wire.

* * * * *